US008557604B2

(12) United States Patent
Song

(10) Patent No.: US 8,557,604 B2
(45) Date of Patent: Oct. 15, 2013

(54) MEMBRANE-BASED LATERAL FLOW ASSAY DEVICES THAT UTILIZE PHOSPHORESCENT DETECTION

(75) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 935 days.

(21) Appl. No.: 11/956,397

(22) Filed: Dec. 14, 2007

(65) Prior Publication Data

US 2008/0090253 A1 Apr. 17, 2008

Related U.S. Application Data

(63) Continuation of application No. 10/718,989, filed on Nov. 21, 2003, now abandoned.

(51) Int. Cl.
*G01N 33/558* (2006.01)

(52) U.S. Cl.
USPC ........... 436/514; 422/401; 422/420; 422/425; 435/287.7; 435/287.9; 435/805; 435/810; 435/970; 436/169; 436/172; 436/518; 436/524; 436/525; 436/531; 436/534; 436/805; 436/810

(58) Field of Classification Search
USPC ......... 436/501, 518, 164, 172, 543, 544, 546; 435/546, 4, 7.1, 287.1, 287.2, 288.7; 422/68.1, 82.05, 82.08, 82.09
See application file for complete search history.

(56) References Cited

U.S. PATENT DOCUMENTS 1,366,241 A 1/1921 Burch
3,604,927 A 9/1971 Hirschfeld
3,700,623 A 10/1972 Keim
3,772,076 A 11/1973 Keim
3,835,247 A 9/1974 Soames
4,006,360 A 2/1977 Mueller
4,094,647 A 6/1978 Deutsch et al.
4,110,529 A 8/1978 Stoy
4,168,146 A 9/1979 Grubb et al.
RE30,267 E 5/1980 Bruschi
4,210,723 A 7/1980 Dorman et al.
4,259,574 A 3/1981 Carr et al.

(Continued)

FOREIGN PATENT DOCUMENTS

DE 10025145 11/2001
EP 0073593 3/1983

(Continued)

OTHER PUBLICATIONS

Fleischer et al., Inorganic and Nuclear Chemistry Letters. 1973. vol. 9, No. 11. pp. 1219-1220.*

(Continued)

*Primary Examiner* — Chris L Chin
(74) *Attorney, Agent, or Firm* — Dority & Manning, P.A.

(57) ABSTRACT

A lateral flow, membrane-based assay device for detecting the presence or quantity of an analyte residing in a test sample is provided. The device utilizes phosphorescence to detect the signals generated by excited phosphorescent labels. The labels may have a long emission lifetime so that background interference from many sources, such as scattered light and autofluorescence, is practically eliminated during detection. In addition, the phosphorescent labels may be encapsulated within particles to shield the labels from quenchers, such as oxygen or water, which might disrupt the phosphorescent signal.

20 Claims, 4 Drawing Sheets

20 50 28 Ic Is 22 32 31 23 21

(56) References Cited

U.S. PATENT DOCUMENTS 4,275,149 A 6/1981 Litman et al.
4,312,228 A 1/1982 Wohltjen
4,336,459 A 6/1982 Fay
4,341,957 A 7/1982 Wieder
4,357,311 A 11/1982 Schutt
4,363,874 A 12/1982 Greenquist
4,366,241 A 12/1982 Tom et al.
4,374,925 A 2/1983 Litman et al.
4,385,126 A 5/1983 Chen et al.
4,426,451 A 1/1984 Columbus
4,427,836 A 1/1984 Kowalski et al.
4,435,504 A 3/1984 Zuk et al.
4,441,373 A 4/1984 White
4,442,204 A 4/1984 Greenquist et al.
4,444,592 A 4/1984 Ludwig
4,477,635 A 10/1984 Mitra
4,480,042 A 10/1984 Craig et al.
4,533,499 A 8/1985 Clark et al.
4,533,629 A 8/1985 Litman et al.
4,534,356 A 8/1985 Papadakis
4,537,657 A 8/1985 Keim
4,537,861 A 8/1985 Blings et al.
4,540,659 A 9/1985 Litman et al.
4,552,458 A 11/1985 Lowne
4,561,286 A 12/1985 Sekler et al.
4,562,157 A 12/1985 Lowe et al.
4,586,695 A 5/1986 Miller
4,595,661 A 6/1986 Cragle et al.
4,596,697 A 6/1986 Ballato
4,614,723 A 9/1986 Schmidt et al.
4,632,559 A 12/1986 Brunsting
4,661,235 A 4/1987 Krull et al.
4,680,275 A * 7/1987 Wagner et al. ................ 436/518
4,698,262 A 10/1987 Schwartz et al.
4,722,889 A 2/1988 Lee et al.
4,727,019 A 2/1988 Valkirs et al.
4,731,337 A 3/1988 Luotola et al.
4,743,542 A 5/1988 Graham, Jr. et al.
4,776,944 A 10/1988 Janata et al.
4,791,310 A 12/1988 Honig et al.
4,818,710 A 4/1989 Sutherland et al.
4,837,168 A 6/1989 de Jaeger et al.
4,842,783 A 6/1989 Blaylock
4,843,000 A 6/1989 Litman et al.
4,843,021 A 6/1989 Noguchi et al.
4,844,613 A 7/1989 Batchelder et al.
4,849,338 A 7/1989 Litman et al.
4,855,240 A 8/1989 Rosenstein et al.
4,857,453 A 8/1989 Ullman et al.
4,877,586 A 10/1989 Devaney, Jr. et al.
4,877,747 A 10/1989 Stewart
4,877,965 A 10/1989 Dandliker et al.
4,895,017 A 1/1990 Pyke et al.
4,916,056 A 4/1990 Brown, III et al.
4,917,503 A 4/1990 Bhattacharjee
4,940,734 A 7/1990 Ley et al.
4,963,498 A 10/1990 Hillman et al.
4,973,670 A 11/1990 McDonald et al.
4,992,385 A 2/1991 Godfrey
5,003,178 A 3/1991 Livesay
5,023,053 A 6/1991 Finlan
5,026,653 A 6/1991 Lee et al.
5,035,863 A 7/1991 Finlan et al.
5,051,162 A 9/1991 Kambara et al.
5,055,265 A 10/1991 Finlan
5,063,081 A 11/1991 Cozzette et al.
5,064,619 A 11/1991 Finlan
5,075,077 A 12/1991 Durley, III et al.
5,076,094 A 12/1991 Frye et al.
5,096,671 A 3/1992 Kane et al.
5,114,676 A 5/1992 Leiner et al.
5,120,662 A 6/1992 Chan et al.
5,124,254 A 6/1992 Hewlins et al.
5,134,057 A 7/1992 Kuypers et al.
5,137,609 A 8/1992 Manian et al.
5,143,854 A 9/1992 Pirrung et al.
5,145,784 A 9/1992 Cox et al.
5,152,758 A 10/1992 Kaetsu et al.
5,156,953 A 10/1992 Litman et al.
5,166,079 A 11/1992 Blackwood et al.
5,179,288 A 1/1993 Miffitt et al.
5,182,135 A 1/1993 Giesecke et al.
5,196,350 A 3/1993 Backman et al.
5,200,084 A 4/1993 Liberti et al.
5,208,535 A 5/1993 Nakayama et al.
5,221,454 A 6/1993 Manian et al.
5,225,935 A 7/1993 Watanabe et al.
5,234,813 A 8/1993 McGeehan et al.
5,235,238 A 8/1993 Nomura et al.
5,238,815 A 8/1993 Higo et al.
5,242,828 A 9/1993 Bergstrom et al.
5,252,459 A 10/1993 Tarcha et al.
5,262,299 A 11/1993 Evangelists et al.
5,268,306 A 12/1993 Berger et al.
5,314,923 A 5/1994 Cooke et al.
5,316,727 A 5/1994 Suzuki et al.
5,320,944 A 6/1994 Okada et al.
5,321,492 A 6/1994 Detwiler et al.
5,327,225 A 7/1994 Bender et al.
5,330,898 A 7/1994 Bar-Or et al.
5,342,759 A 8/1994 Litman et al.
5,352,582 A 10/1994 Lichtenwalter et al.
5,356,782 A 10/1994 Moorman et al.
5,358,852 A 10/1994 Wu
5,369,717 A 11/1994 Attridge
5,374,563 A 12/1994 Maule
5,376,255 A 12/1994 Gumbrecht et al.
5,387,503 A 2/1995 Selmer et al.
5,395,754 A 3/1995 Lambotte et al.
5,415,842 A 5/1995 Maule
5,418,136 A 5/1995 Miller et al.
5,424,219 A 6/1995 Jirikowski
5,424,841 A 6/1995 Van Gelder et al.
5,432,057 A 7/1995 Litman et al.
5,436,161 A 7/1995 Bergstrom et al.
5,445,971 A 8/1995 Rohr
5,451,683 A 9/1995 Barrett et al.
5,455,475 A 10/1995 Josse et al.
5,464,741 A 11/1995 Hendrix
5,466,574 A 11/1995 Liberti et al.
5,467,778 A 11/1995 Catt et al.
5,468,606 A 11/1995 Bogart et al.
5,482,830 A 1/1996 Bogart et al.
5,482,867 A 1/1996 Barrett et al.
5,484,867 A 1/1996 Lichtenham et al.
5,489,678 A 2/1996 Fodor et al.
5,489,988 A 2/1996 Ackley et al.
5,492,840 A 2/1996 Malmqvist et al.
5,496,701 A 3/1996 Pollard-Knight
5,500,350 A 3/1996 Baker et al.
5,504,013 A 4/1996 Senior
5,508,171 A 4/1996 Walling et al.
5,510,481 A 4/1996 Bednarski et al.
5,512,131 A 4/1996 Kumar et al.
5,514,559 A 5/1996 Markert-Hahn et al.
5,514,785 A 5/1996 Van Ness et al.
5,516,635 A 5/1996 Ekins et al.
5,518,689 A 5/1996 Dosmann et al.
5,518,883 A 5/1996 Soini
5,527,711 A 6/1996 Tom-Moy et al.
5,534,132 A 7/1996 Vreeke et al.
5,554,539 A 9/1996 Chadney et al.
5,554,541 A 9/1996 Malmqvist et al.
5,569,608 A 10/1996 Sommer
5,571,684 A 11/1996 Lawrence et al.
5,573,909 A 11/1996 Singer et al.
5,585,279 A 12/1996 Davidson
5,589,401 A 12/1996 Hansen et al.
5,591,581 A 1/1997 Massey et al.
5,596,414 A 1/1997 Tyler
5,599,668 A 2/1997 Stimpson et al.
5,618,888 A 4/1997 Choi et al.
5,620,850 A 4/1997 Bamdad et al.
5,637,509 A 6/1997 Hemmilä et al.

(56) References Cited

U.S. PATENT DOCUMENTS 5,647,994 A 7/1997 Tuunanen et al.
5,658,443 A 8/1997 Yamamoto et al.
5,663,213 A 9/1997 Jones et al.
5,670,381 A 9/1997 Jou et al.
5,672,256 A 9/1997 Yee
5,674,698 A 10/1997 Zarling et al.
5,700,636 A 12/1997 Sheiness et al.
5,723,294 A 3/1998 Glass et al.
5,726,064 A 3/1998 Robinson et al.
5,731,147 A 3/1998 Bard et al.
5,736,188 A 4/1998 Alcock et al.
5,753,517 A 5/1998 Brooks et al.
5,770,416 A 6/1998 Lihme et al.
5,780,251 A 7/1998 Klainer et al.
5,780,308 A 7/1998 Ching et al.
5,795,470 A 8/1998 Wang et al.
5,795,543 A 8/1998 Poto et al.
5,798,273 A 8/1998 Shuler et al.
5,811,526 A 9/1998 Davidson
5,827,748 A 10/1998 Golden
5,830,762 A 11/1998 Weindel
5,832,165 A 11/1998 Reichert et al.
5,834,226 A 11/1998 Maupin
5,837,429 A 11/1998 Nohr et al.
5,837,546 A 11/1998 Allen et al.
5,843,692 A 12/1998 Phillips et al.
5,852,229 A 12/1998 Josse et al.
5,876,944 A 3/1999 Kuo
5,879,881 A 3/1999 Rubenstein
5,885,527 A 3/1999 Buechler
5,906,921 A 5/1999 Ikeda et al.
5,910,286 A 6/1999 Lipskier
5,910,447 A 6/1999 Lawrence et al.
5,910,940 A 6/1999 Guerra
5,922,537 A 7/1999 Ewart et al.
5,922,550 A 7/1999 Everhart et al.
5,943,129 A 8/1999 Hoyt et al.
5,951,492 A 9/1999 Douglas et al.
5,962,995 A 10/1999 Avnery
6,004,530 A 12/1999 Sagner et al.
6,008,892 A 12/1999 Kain et al.
6,020,047 A 2/2000 Everhart
6,027,904 A 2/2000 Devine et al.
6,027,944 A 2/2000 Robinson et al.
6,030,792 A 2/2000 Otterness et al.
6,030,840 A 2/2000 Mullinax et al.
6,033,574 A 3/2000 Siddiqi
6,048,623 A 4/2000 Everhart et al.
6,060,256 A 5/2000 Everhart et al.
6,080,391 A 6/2000 Tsuchiya et al.
6,084,683 A 7/2000 Bruno et al.
6,087,184 A 7/2000 Magginetti et al.
6,099,484 A 8/2000 Douglas et al.
6,103,537 A 8/2000 Ullman et al.
6,117,090 A 9/2000 Caillouette
6,136,549 A 10/2000 Feistel
6,136,611 A 10/2000 Saaski et al.
6,139,961 A 10/2000 Blankenship et al.
6,151,110 A 11/2000 Markart
6,165,798 A 12/2000 Brooks
6,171,780 B1 1/2001 Pham et al.
6,171,870 B1 1/2001 Freitag
6,174,646 B1 1/2001 Hirai et al.
6,177,281 B1 1/2001 Manita
6,180,288 B1 1/2001 Everhart et al.
6,183,972 B1 2/2001 Kuo et al.
6,184,042 B1 2/2001 Neumann et al.
6,194,220 B1 2/2001 Malick et al.
6,200,820 B1 3/2001 Hansen et al.
6,221,238 B1 4/2001 Grundig et al.
6,221,579 B1 4/2001 Everhart et al.
6,234,974 B1 5/2001 Catt et al.
6,235,241 B1 5/2001 Catt et al.
6,235,471 B1 5/2001 Knapp et al.
6,235,491 B1 5/2001 Connolly
6,241,863 B1 6/2001 Monbouquette
6,242,268 B1 6/2001 Wieder et al.
6,255,066 B1 7/2001 Louderback
6,261,779 B1 7/2001 Barbera-Guillem et al.
6,268,222 B1 7/2001 Chandler et al.
6,270,637 B1 8/2001 Crismore et al.
6,271,040 B1 8/2001 Buechler
6,281,006 B1 8/2001 Heller et al.
6,284,472 B1 9/2001 Wei et al.
6,287,783 B1 9/2001 Maynard et al.
6,287,871 B1 9/2001 Herron et al.
6,294,392 B1 9/2001 Kuhr et al.
6,306,665 B1 10/2001 Buck et al.
D450,854 S 11/2001 Lipman et al.
6,316,466 B1 11/2001 Goldstein et al.
6,331,438 B1 12/2001 Aylott et al.
6,348,186 B1 2/2002 Sutton et al.
6,362,011 B1 3/2002 Massey et al.
6,368,873 B1 4/2002 Chang et al.
6,368,875 B1 4/2002 Geisberg
6,387,707 B1 5/2002 Seul et al.
6,391,558 B1 5/2002 Henkens et al.
6,396,053 B1 5/2002 Yokoi
6,399,295 B1 6/2002 Kaylor et al.
6,399,397 B1 6/2002 Zarling et al.
6,403,384 B1 6/2002 Lea
6,407,492 B1 6/2002 Avnery et al.
6,411,439 B2 6/2002 Nishikawa
6,413,410 B1 7/2002 Hodges et al.
6,436,651 B1 8/2002 Everhart et al.
6,436,722 B1 8/2002 Clark et al.
6,444,423 B1 9/2002 Meade et al.
6,448,091 B1 9/2002 Massey et al.
6,451,607 B1 9/2002 Lawrence et al.
6,455,861 B1 9/2002 Hoyt
6,461,496 B1 10/2002 Feldman et al.
6,468,741 B1 10/2002 Massey et al.
6,472,226 B1 10/2002 Barradine et al.
6,473,239 B1 10/2002 Volcker et al.
6,479,146 B1 11/2002 Caruso et al.
6,483,582 B2 11/2002 Modlin et al.
6,498,690 B2 12/2002 Ramm et al.
6,509,085 B1 1/2003 Kennedy
6,509,196 B1 1/2003 Brooks et al.
6,511,814 B1 1/2003 Carpenter
6,556,299 B1 4/2003 Rushbrooke et al.
6,566,508 B2 5/2003 Bentsen et al.
6,573,040 B2 6/2003 Everhart et al.
6,579,673 B2 6/2003 McGrath et al.
6,582,930 B1 * 6/2003 Ponomarev et al. ......... 435/40.5
6,585,939 B1 7/2003 Dapprich
6,607,922 B2 8/2003 LaBorde
6,613,583 B1 9/2003 Richter et al.
6,617,488 B1 9/2003 Springer et al.
6,660,379 B1 12/2003 Lakowicz et al.
6,665,072 B2 12/2003 Hoyt
6,670,115 B1 12/2003 Zhang
6,699,722 B2 3/2004 Bauer et al.
6,720,007 B2 4/2004 Walt et al.
6,770,220 B1 8/2004 Klimant
6,787,368 B1 9/2004 Wong et al.
6,815,218 B1 11/2004 Jacobson et al.
6,867,851 B2 3/2005 Blumenfeld et al.
6,916,666 B1 7/2005 Mendel-Hartvig et al.
7,255,998 B1 8/2007 Tashiro et al.
2001/0036645 A1 11/2001 McNeirney et al.
2001/0055776 A1 12/2001 Greenwalt
2002/0004246 A1 1/2002 Daniels et al.
2002/0031839 A1 3/2002 McNeirney et al.
2002/0052048 A1 5/2002 Stein et al.
2002/0070128 A1 6/2002 Beckmann
2002/0132370 A1 9/2002 Lassen et al.
2002/0146754 A1 10/2002 Kitawaki et al.
2002/0164659 A1 11/2002 Rao et al.
2002/0166764 A1 11/2002 MacPhee
2002/0167662 A1 11/2002 Tanaami et al.
2002/0177235 A1 11/2002 Mabile et al.
2003/0017615 A1 1/2003 Sidwell et al.
2003/0108949 A1 6/2003 Bao et al.

(56) References Cited

U.S. PATENT DOCUMENTS

2003/0119202 A1 6/2003 Kaylor et al.
2003/0119204 A1* 6/2003 Wei et al. ...................... 436/514
2003/0124739 A1 7/2003 Song et al.
2003/0157727 A1 8/2003 Nagano et al.
2003/0162236 A1 8/2003 Harris et al.
2003/0178309 A1 9/2003 Huang et al.
2004/0014073 A1 1/2004 Trau et al.
2004/0043502 A1 3/2004 Song et al.
2004/0043507 A1 3/2004 Song et al.
2004/0043511 A1 3/2004 Song et al.
2004/0043512 A1 3/2004 Song et al.
2004/0096991 A1 5/2004 Zhang
2004/0106190 A1 6/2004 Yang et al.
2004/0130715 A1 7/2004 Dosaka et al.
2004/0132122 A1 7/2004 Banerjee et al.
2005/0032051 A1 2/2005 Hayes et al.

FOREIGN PATENT DOCUMENTS

EP 0420053 4/1991
EP 0469377 2/1992
EP 0617285 9/1994
EP 0703454 3/1996
EP 0462376 7/1996
EP 0724156 7/1996
EP 0745843 12/1996
EP 0898169 2/1999
EP 0711414 3/1999
EP 1253427 A2 10/2002
EP 1253427 A3 10/2002
JP 8062214 3/1996
WO WO 8804777 6/1988
WO WO 9105999 5/1991
WO WO 9221769 12/1992
WO WO 9221770 12/1992
WO WO 9221975 12/1992
WO WO 9301308 1/1993
WO WO 9413835 6/1994
WO WO 9709620 * 3/1997
WO WO 9930131 6/1999
WO WO 9964864 12/1999
WO WO 0023805 4/2000
WO WO 0205698 1/2002

OTHER PUBLICATIONS

Abstract of EP 0711414, published Mar. 10, 1999.
Abstract of JP 8062214, published Mar. 8, 1996.
Abstract of Article—*Factors influencing the formation of hollow ceramic microspheres by water extraction of colloidal droplets*, J. Mater. Res., vol. 10, No. 1, p. 84.
Article—*A conductometric biosensor for biosecurity*, Zarini Muhammid-Tahir and Evangelyn C. Alocilja, Biosensors and Bioelectronics 18, 2003, pp. 813-819.
Article—*A Disposable Amperometric Sensor Screen Printed on a Nitrocellulose Strip: A Glucose Biosensor Employing Lead Oxide as an Interference-Removing Agent*, Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.
Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.
Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.
Article—*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp. 4247-4249.
Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.
Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.
Article—*Analysis of electrical equivalent circuit of quartz crystal resonator loaded with viscous conductive liquids*, Journal of Electroanalytical Chemistry, vol. 379, 1994, pp. 21-33.
Article—*Application of rod-like polymers with ionophores as Langmuir-Blodgett membranes for Si-based ion sensors*, Sensors and Actuators B, 1992, pp. 211-216.
Article—*Attempts to Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.
Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.
Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.
Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.
Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.
Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.
Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.
Article—*Fabrication of Patterned, Electrically Conducting Polypyrrole Using a Self-Assembled Monolayer: A Route to All-Organic Circuits*, Christopher B. Gorman, Hans A. Biebuyck, and George M. Whitesides, American Chemical Society, 2 pages.
Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.
Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.
Article—*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.
Article—Flow-*Based Microimmunoassay*, Analytical Chemistry, vol. 73, No. 24, Mark A. Hayes, Nolan A. Poison, Allison, N. Phayre, and Antonia A. Garcia, Dec. 15, 2001, pp. 5896-5902.
Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.
Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

(56) References Cited

OTHER PUBLICATIONS

Article—*Hollow latex particles: synthesis and applications*, Charles J. McDonald and Michael J. Devon, Advances in Colloid and Interface Science, Vo. 99, 2002, pp. 181-213.
Article—*How to Build a Spectrofluorometer*, Spex Fluorolog 3, Horiba Group, pp. 1-14.
Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.
Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.
Article—*Inert Phosphorescent Nanospheres as Markers for Optical Assays*, Jens M. Kümer, Ingo Klimant, Christian Krause, Harald Preu, Werner Kunz, and Otto S. Wolfbeis, Bioconjugate Chem., vol. 12, No. 6, 2001, pp. 883-889.
Article—*Intelligent Gels*, Yoshihito Osada and Simon B. Ross-Murphy, Scientific American, May 1993, pp. 82-87.
Article—*Latex Immunoassays*, Leigh B. Bangs, Journal of Clinical Immunoassay, vol. 13, No. 3, 1990, pp. 127-131.
Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.
Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.
Article—*Microfabrication by Microcontact Printing of Self-Assembled Monolyaers*, James L. Wilbur, Armit Kumar, Enoch Kim, and George M. Whitesides, Advanced Materials, vol. 6, No. 7/8, 1994, pp. 600-604.
Article—*Modification of monoclonal and polyclonal IgG with palladium (II) coproporphyrin I: stimulatory and inhibitory functional effects induced by two different methods*, Sergey P. Martsev, Valery A. Preygerzon, Yanina I. Mel'nikova, Zinaida I. Kravchuk, Gely V. Ponomarev, Vitaly E. Lunev, and Alexander P. Savitsky, Journal of Immunological Methods 186, 1996, pp. 293-304.
Article—*Molecular Design Temperature-Responsive Polymers as Intelligent Materials*, Teruo Okano, Advances in Polymer Science, pp. 179-197.
Article—*Molecular Gradients of w-Substituted Alkanethiols on Gold: Preparation and Characterization*, Bo Liedberg and Pentti Tengvall, Langmuir, vol. 11, No. 10, 1995, pp. 3821-3827.
Article—*Monofunctional Derivatives of Coproporphyrins for Phosphorescent Labeling of Proteins and Binding Assays*, Tomás C. O'Riordan, Aleksi E. Soini, and Dmitri B. Papkovsky, Analytical Biochemistry, vol. 290, 2001, pp. 366-375.
Article—*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.
Article—*Near Infrared Phosphorescent Metalloporphrins*, Alexander P. Savitsky Anna V. Savitskaja, Eugeny A. Lukjanetz, Svetlana N. Dashkevich, and Elena A. Makarova, SPIE, vol. 2980, pp, 352-357.
Article—*New Approach to Producing Patterned Biomolecular Assemblies*, Suresh K. Bhatia, James J. Hickman, and Frances S. Ligler, J. Am. Chem. Soc., vol. 114, 1992, pp. 4433-4434.
Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.
Article—*On the use of ZX-LiNbO$_3$ acoustic plate mode devices as detectors for dilute electrolytes*, F. Josse, Z. A. Shana, D. T. Haworth, and S. Liew, Sensors and Actuators B, vol. 9, 1992, pp. 92-112.
Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.
Article—*Optical Biosensor Assay* (*OBA*™), Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.
Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.
Article—*Orientation dependence of surface segregation in a dilute Ni-Au alloy*, W. C. Johnson, N. G. Chavka, R. Ku, J. L. Bomback, and P. P. Wynblatt, J. Vac. Sci. Technol. vol. 15, No. 2, Mar./Apr. 1978, pp. 467-469.
Article—*Patterned Condensation Figures as Optical Diffraction Gratings*, Amit Kumar and George M. Whitesides, Science, vol. 263, Jan. 7, 1994, pp. 60-62.
Article—*Patterned Functionalization of Gold and Single Crystal Silicon via Photochemical Reaction of Surface-Confined Derivatives of* ($n^5$-$C_5H_5$)$Mn(CO)_3$, Doris Kang and Mark S. Wrighton, Langmuir, vol. 7, No. 10, 1991, pp. 2169-2174.
Article—*Patterned Metal Electrodeposition Using an Alkanethiolate Mask*, T. P. Moffat and H. Yang, J. Electrochem. Soc., vol. 142, No. 11, Nov. 1995, pp. L220-L222.
Article—*Performance Evaluation of the Phosphorescent Porphyrin Label: Solid-Phase Immunoassay of α-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.
Article—*Phosphorescent porphyrin probes in biosensors and sensitive bioassays*, D. B. Papkovsky, T. O'Riordan, and A. Soini, Biochemical Society Transactions, vol. 28, part 2, 2000, pp. 74-77.
Article—*Photolithography of self-assembled monolayers: optimization of protecting groups by an electroanalytical method*, Jamila Jennane, Tanya Boutrous, and Richard Giasson, Can. J. Chem., vol. 74, 1996, pp. 2509-2517.
Article—*Photopatterning and Selective Electroless Metallization of Surface-Attached Ligands*, Walter J. Dressick, Charles S. Dulcey, Jacque H. Georger, Jr., and Jeffrey M. Calvert, American Chemical Society, 2 pages.
Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.
Article—*Polymer Based Lanthanide Luminescent Sensors for the Detection of Nerve Agents*, Amanda L. Jenkins, O. Manuel Uy, and George M. Murray, Analytical Communications, vol., 34, Aug. 1997, pp. 221-224.
Article—*Prediction of Segregation to Alloy Surfaces from Bulk Phase Diagrams*, J. J. Burton and E. S. Mechlin, Physical Review Letters, vol. 37, No. 21, Nov. 22, 1976, pp. 1433-1436.
Article—*Principle and Applications of Size-Exclusion Chromatography*, Impact Analytical, pp. 1-3.
Article—*Probing of strong and weak electrolytes with acoustic wave fields*, R. Dahint, D. Grunze, F. Josse, and J. C. Andle, Sensors and Actuators B, vol. 9, 1992, pp. 155-162.
Article—*Production of Hollow Microspheres from Nanostructured Composite Particles*, Frank Caruso, Rachel A. Caruso, and Helmuth MöthwaldChem, Mater., vol. 11, No. 11, 1999, pp. 3309-3314.
Article—*Quantitative Prediction of Surface Segregation*, M. P. Seah, Journal of Catalysts, vol. 57, 1979, pp. 450-457.
Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.
Article—*Responsive Gels: Volume Transitions I*, M. Ilayský, H. Inomata, A. Khokhlove, M. Konno, A. Onuki, S. Saito, M.

(56) References Cited

OTHER PUBLICATIONS

Shibayama, R.A. Siegel, S. Starodubtzev, T. Tanaka, and V. V. Vasiliveskaya, Advances in Polymer Science, vol. 109, 9 pages.
Article—*Room-Temperature Phosphorescent Palladium—Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.
Article—*Self-Assembled Monolayer Films for Nanofabrication*, Elizabeth A. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.
Article—*Sensing liquid properties with thickness-shear mode resonators*, S. J. Martin, C. Frye, and K. O. Wessendorf, Sensors and Actuators A, vol. 44, 1994, pp. 209-218.
Article—*Separation-Free Sandwich Enzyme Immunoassays Using Microporous Gold Electrodes and Self-Assembled Monolayer/Immobolized Capture Antibodies*, Chuanming Duan and Mark E. Meyerhoff, Analytical Chemistry, vol. 66, No. 9, May 1, 1994, pp. 1369-1377.
Article—*Solid Substrate Phosphorescent Immunoassay Based on Bioconjugated Nanoparticles*, Baoquan Sun, Guangshum Yi, Shuying Zhao, Depu Chen, Yuxiang Zhou and Jing Cheng, Analytical Letters, vol. 34, No. 10, 2001, pp. 1627-1637.
Article—*Stimuli-Responsive Poly(N-isopropylacrylamide) Photo- and Chemical-Induced Phase Transitions*, Advances in Polymer Science, pp. 50-65.
Article—*The Adsorptive Characteristics of Proteins for Polystyrene and Their Significance in Solid-Phase Immunoassays*, L. A. Cantaero, J. E. Butler, and J. W. Osborne, Analytical Biochemistry, vol. 105, 1980, pp. 375-382.
Article—*The Use of Self-Assembled Monolayers and a Selective Etch to Generate Patterned Gold Features*, Amit Kumar, Hans A. Biebuyck, Nicholas L. Abbott, and George M. Whitesides, Journal of the American Chemical Society, vol. 114, 1992, 2 pages.
Article—*Volume Phase Transition of N-Alkylacrylamide Gels*, S. Saito, M. Konno, and Inomata, Advances in Polymer Science, vol. 109, 1992, pp. 207-232.
Article—*Whole Blood Capcellia CD4/CD8 Immunoassay for Enumeration of CD4+ and CD8+ Peripheral T Lymphocytes*, Dominique Corrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.
8 Photographs of Accu-chek® Blood Glucose Meter.
*AMI Screen Printers*—Product Information, 4 pages.
*CELQUAT® SC-230M (28/6830)*, CELQUAT® SC-240C and SC-230M, from National Starch & Chemical, 1 page.
*CELQUAT® SC-230M (28/6830)*, Polyquaternium-10, from National Starch & Chemical, 1 page.
*Dualite® Polymeric Microspheres*, from Pierce & Stevens Corp. A subsidiary of Sovereign Specialty Chemicals, Inc., 2 pages.
*Dynabeads® Biomagnetic Separation Technology—The Principle* from Dynal Biotech, 2 pages.
*ECCOSPHERES® glass microspheres—hollow glass microspheres* from Emerson & Cuming Composite Materials, Inc., 1 page.
*Fluorescence Microplate Assays*, Product Description from Molecular Probes, 112 pages.
*Fluorescent Microsphere Standards for Flow Cytometry and Fluorescence Microscopy* from Molecular Probes, pp. 1-8.
*FluoSpheres® Fluorescent Microspheres*, Product Information from Molecular Probes, Mar. 13, 2001, pp. 1-6.
*Magnetic Microparticles*, Polysciences, Inc. Technical Data Sheet 438, 2 pages.
*Making sun exposure safer for everyone* from Rohm and Haas Company (Bristol Complex), 2 pages.
Pamphlet—The ClearPlan® Easy Fertility Monitor.
*POSS Polymer Systems* from Hybrid Plastics, 3 pages.
*The colloidal state*, Introduction to Colloid and Surface Chemistry, $4^{th}$ Ed., 17 pages.
*Working With FluoSpheres® Fluorescent Microspheres*, Properties and Modifications, Product Information from Molecular Probes, Mar. 9, 2001, pp. 1-5.
Machine Translation of German Publication No. DE10025145A, 4 pages.

* cited by examiner

MEMBRANE-BASED LATERAL FLOW ASSAY DEVICES THAT UTILIZE PHOSPHORESCENT DETECTION

CROSS-REFERENCE TO RELATED APPLICATIONS

The present application claims priority to and is a continuation application of application Ser. No. 10/718,989, filed on Nov. 21, 2003, which is incorporated herein by reference in its entirety.

BACKGROUND OF THE INVENTION

Phosphorescence is the result of a three-stage process. In the first stage, energy is supplied by an external source, such as an incandescent lamp or a laser, and absorbed by the phosphorescent compound, creating excited electronic triplet states (as opposed to fluorescence, which only has a singlet excited state). In the second stage, the excited states exist for a finite time during which the phosphorescent compound undergoes conformational changes and is also subject to a multitude of possible interactions with its molecular environment. During this time, the energy of the excited states is partially dissipated, yielding relaxed states from which phosphorescence emission originates. The third stage is the phosphorescence emission stage wherein energy is emitted, returning the phosphorescence compound to its ground states. The emitted energy is lower than its excitation energy (light or laser) and thus of a longer wavelength. This shift or difference in energy or wavelength allows the emission energy to be detected and isolated from the excitation energy.

Various phosphorescent compounds, such as metalloporphyrins, have been proposed for use in immunoassays. Unfortunately, many of the proposed techniques fail to solve the problem of quenching. Specifically, oxygen and water are strong quenchers of triplet states and may cause decay of the phosphorescence signal, thereby limiting its use in most practical assay applications. In addition, many of the techniques that have been proposed are simply ill equipped for use in lateral flow, membrane-based devices. For example, in a lateral flow, membrane-based assay device, the concentration of the analyte is reduced because it is diluted by a liquid that may flow through the porous membrane. However, background interference becomes increasingly problematic at such low analyte concentrations because the phosphorescent intensity is relatively low. Because the structure of the membrane also tends to reflect the excited light, the ability of a detector to accurately measure the phosphorescent intensity of the labeled analyte is substantially reduced. In fact, the intensity of the emitted phosphorescence signal may be three to four orders of magnitude smaller than the excitation light reflected by the porous membrane. Many membranes, such as nitrocellulose membranes, also exhibit strong fluorescence when excited in the UV and visible regions. This fluorescence can interfere with the accuracy of phosphorescence measurements.

As such, a need currently exists for a simple, inexpensive, and effective system for using phosphorescence as a detection technique for membrane-based, lateral flow assay devices.

SUMMARY OF THE INVENTION

In accordance with one embodiment of the present invention, a method for detecting the presence or quantity of an analyte residing in a test sample is disclosed. The method comprises:

i) providing a lateral flow assay device that comprises a porous membrane in fluid communication with detection probes, the detection probes comprising a phosphorescent label encapsulated within a matrix, wherein the porous membrane defines a detection zone within which is immobilized a capture reagent that is configured to bind to the detection probes or complexes thereof;

ii) contacting the detection probes with the test sample;

iii) allowing the detection probes and the test sample to flow to the detection zone;

iv) exciting the phosphorescent label at the detection zone to generate an emitted detection signal; and v) measuring the intensity of the detection signal, wherein the amount of the analyte within the test sample is proportional to the intensity of the detection signal.

In accordance with another embodiment of the present invention, a lateral flow assay device for detecting the presence or quantity of an analyte residing in a test sample is disclosed. The assay device comprises a porous membrane in fluid communication with detection probes. The detection probes comprise a phosphorescent metal complex encapsulated within a matrix. The porous membrane defines a detection zone within which a capture reagent is immobilized that is configured to bind to the detection probes or complexes thereof to generate a detection signal, wherein the amount of the analyte in the test sample is proportional to the intensity of the detection signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
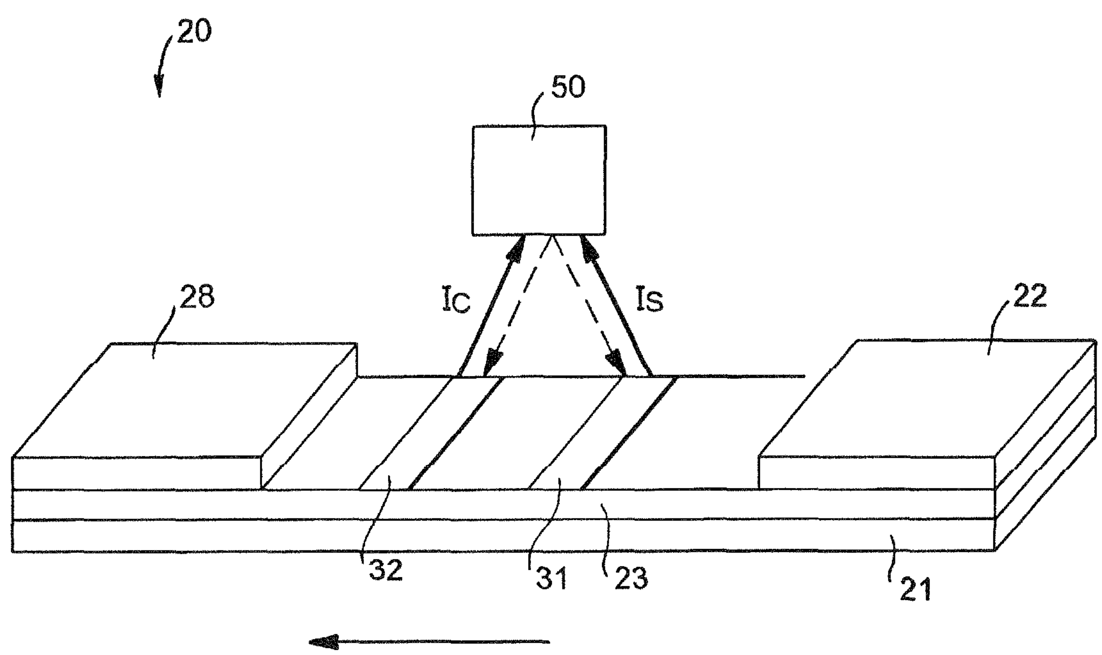
FIG. 1 is a perspective view of one embodiment of a lateral flow, membrane-based device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenyloin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a material suspected of containing the analyte. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. The test sample may be pretreated prior to use, such as preparing plasma from blood, diluting viscous fluids, and the like. Methods of treatment may involve filtration, precipitation, dilution, distillation, mixing, concentration, inactivation of interfering components, and the addition of reagents. Besides physiological fluids, other liquid samples may be used such as water, food products and the like for the performance of environmental or food production assays. In addition, a solid material suspected of containing the analyte may be used as the test sample. In some instances it may be beneficial to modify a solid test sample to form a liquid medium or to release the analyte.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a lateral flow, membrane-based assay device for detecting the presence or quantity of an analyte residing in a test sample. The device utilizes phosphorescence to detect the signals generated by excited phosphorescent labels. The labels may have a long emission lifetime so that background interference from many sources, such as scattered light and autofluorescence, is practically eliminated during detection. In addition, the phosphorescent labels may be encapsulated within particles to shield the labels from quenchers, such as oxygen or water, which might disrupt the phosphorescent signal.

Referring to FIG. 1, for instance, one embodiment of a flow-through assay device 20 that may be formed according to the present invention will now be described in more detail. As shown, the device 20 contains a porous membrane 23 optionally supported by a rigid material 21. In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 may assist in promoting capillary action and fluid flow through the membrane 23.

To initiate the detection of an analyte within the test sample, a user may directly apply the test sample to a portion of the porous membrane 23 through which it may then travel. Alternatively, the test sample may first be applied to a sampling pad (not shown) that is in fluid communication with the porous membrane 23. Some suitable materials that may be used to form the sampling pad include, but are not limited to, nitrocellulose, cellulose, porous polyethylene pads, and glass fiber filter paper. If desired, the sampling pad may also contain one or more assay pretreatment reagents, either diffusively or non-diffusively attached thereto.

In the illustrated embodiment, the test sample travels from the sampling pad (not shown) to a conjugate pad 22 that is placed in communication with one end of the sampling pad. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used in the present invention.

To facilitate accurate detection of the presence or absence of an analyte within the test sample, labels are applied at various locations of the device 20. The labels may be used for both detection of the analyte and for calibration. Generally speaking, at least a portion of the labels used in the device 20 contain a phosphorescent compound. In general, such phosphorescent compounds may be phosphorescent molecules, polymers, dendrimers, particles, and so forth. In one particular embodiment, for example, the phosphorescent compound is a metal complex that includes one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium.

The metal complex may contain one or more ligands that facilitate the solubility of the complex in an aqueous or non-aqueous environments. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

For example, porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc (II)-coproporphyrin-I, derivatives thereof, and so forth. Similarly, some suitable porphine complexes that are capable of exhibiting phosphorescent properties include, but not limited to, platinum (II) tetra-meso-fluorophenylporphine and palladium (II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

As indicated above, bipyridine metal complexes may also be utilized in the present invention. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium (II); bis(2,2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid] ruthenium (II); tris(2,2'bipyridine)ruthenium (II); (2,2'-bipyridine) [bis-bis(1,2-diphenylphosphino)ethylene] 2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2,2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; 5,731,147 to Bard, et al.; and U.S. Pat. No. 5,591,581 to Massey, et al., which are incorporated herein in their entirety by reference thereto for all purposes.

Regardless of the type of phosphorescent label utilized, the exposure of the label to quenchers, such as oxygen or water, may result in a disruption of the phosphorescent signal. Thus, to ensure that the phosphorescent labels are capable of emitting the desired signal intensity, they are generally encapsulated within a matrix that acts as a barrier to the relevant quencher. For instance, in some embodiments, the matrix may have a low solubility in water and oxygen, and also be relatively impermeable to water and oxygen. In this manner, the phosphorescent label may be protected from emission decay that would otherwise result from exposure to oxygen or water. For example, the matrix may protect the label such that less than about 30%, in some embodiments less than about 20%, and in some embodiments, less than about 10% of the total phosphorescent signal is quenched when the detection probes are exposed to a particular quencher.

Various types of barrier matrices may be employed in the present invention to inhibit quenching of the phosphorescent compounds. For example, in some embodiments, the phosphorescent compound may be encapsulated within a particle. Some suitable particles that may be suitable for this purpose include, but not limited to, metal oxides (e.g., silica, alumina, etc.), polymer particles, and so forth. For example, latex polymer particles may be utilized, such as those formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, derivatives thereof, etc. Other suitable particles may be described in U.S. Pat. No. 5,670,381 to Jou, et al. and U.S. Pat. No. 5,252,459 to Tarcha, et al., which are incorporated herein in their entirety by reference thereto for all purposes.

The phosphorescent compound may be encapsulated within the particulate matrix during and/or after particle formation. In one embodiment, encapsulated latex particles are formed through well-known precipitation techniques. For example, polymer particles may be co-dissolved with the phosphorescent compound in an organic solvent. Thereafter, another solvent may then be added to co-precipitate both the phosphorescent molecules and polymer particles. Some examples of suitable solvents that may be used in such a co-precipitation process include, but are not limited to, water, acetone, acetonitrile, tetrahydrofuran, methylene chloride, cyclohexane, chloroform, ethyl ether, propyl ether, methyl acetate, methyl alcohol, ethyl alcohol, propyl alcohol, pentane, pentene, hexane, methyl ethyl ketone, and other similar solvents.

Besides precipitation, other techniques for forming encapsulated phosphorescent particles may also be used in the present invention. In one embodiment, for example, latex-based phosphorescent particles are formed using swelling techniques. Specifically, a polymer particle is swelled with a swelling agent containing one or more volatile components and phosphorescent molecules. When swollen, the phosphorescent compound may permeate through the polymer particles and become encapsulated therein. Removal of the swelling solvent results in the encapsulated particles. Emulsion polymerization may also be used to form phosphorescent particles. For example, monomers covalently tagged with a phosphorescent moiety may be co-polymerized with other monomers to form phosphorescent particles.

Regardless of the technique by which they are formed, the shape of the encapsulated phosphorescent particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have a average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

In one embodiment of the present invention, the encapsulated phosphorescent particles form detection probes that are used to detect the presence or absence of an analyte within a test sample. In some instances, it is desired to modify the detection probes in some manner so that they are more readily able to bond to the analyte. In such instances, the detection probes may be modified with certain specific binding members to form conjugated detection probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies, and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin, biotin and streptavidin, antibody-binding proteins (such as protein A or G) and antibodies, carbohydrates and lectins, complementary nucleotide sequences (including label and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the detection probes using any of a variety of well-known techniques. For instance, covalent attachment of the specific binding members to the particles may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the particle may contain a relatively high surface concentration of polar groups. In addition, although particles are often functionalized after synthesis, in certain cases, such as poly(thiophenol), the particles are capable of direct covalent linking with a protein without the need for further modification. For example, in one embodiment, the first step of conjugation is activation of carboxylic groups on the particle surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). As shown, the resulting particles may then be blocked with ethanolamine, for instance, to form the conjugated probe. Besides covalent bonding, other attachment techniques, such as physical adsorption, may also be utilized in the present invention.

In general, a variety of flow-through assay devices may be constructed according to the present invention for use in conjunction with a phosphorescence detection system. In this regard, various embodiments of the present invention will now be described in more detail. It should be understood, however, that the embodiments discussed below are only exemplary, and that other embodiments are also contemplated by the present invention. For instance, referring again to FIG. 1, one system for detecting the presence of an analyte within a test sample is schematically illustrated. Initially, a test sample containing an analyte is applied to the sampling pad (not shown). From the sampling pad, the test sample may then travel to the conjugate pad 22, where the analyte mixes with detection probes to form analyte complexes. In one embodiment, for example, the detection probes are formed from microparticles that encapsulate a porphyrin or porphine dye, such as described above, and bound to a specific binding member for the analyte of interest. Moreover, because the conjugate pad 22 is in fluid communication with the porous membrane 23, the complexes may migrate from the conjugate pad 22 to a detection zone 31 present on the porous membrane 23.

The detection zone 31 may contain an immobilized capture reagent that is generally capable of forming a chemical or physical bond with the detection probes. In some embodiments, the capture reagent may be a biological capture reagent. Such biological capture reagents are well known in the art and may include, but are not limited to, antigens, haptens, protein A or G, neutravidin, avidin, streptavidin, captavidin, antibodies (e.g., polyclonal, monoclonal, etc.), and complexes thereof. The immobilized capture reagents serve as stationary binding sites for probe conjugate/analyte complexes. In some instances, the analytes, such as antibodies, antigens, etc., have two binding sites. Upon reaching the detection zone 31, one of these binding sites is occupied by the specific binding member of the complexed detection probes. However, the free binding site of the analyte may bind to the immobilized capture reagent. Upon being bound to the immobilized capture reagent, the complexed detection probes form a new ternary sandwich complex.

The detection zone 31 may generally provide any number of distinct detection regions so that a user may better determine the concentration of a particular analyte within a test sample. Each region may contain the same capture reagents, or may contain different capture reagents for capturing multiple analytes. For example, the detection zone 31 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions may be disposed in the form of lines in a direction that is substantially parallel to the flow of the test sample through the assay device.

Although the detection zone 31 may indicate the presence of an analyte, it is often difficult to determine the relative concentration of the analyte within the test sample using solely a detection zone 31. Thus, the assay device 20 may also include a calibration zone 32. In this embodiment, the calibration zone 32 is formed on the porous membrane 23 and is positioned downstream from the detection zone 31, although it may also be positioned upstream if desired. The calibration zone 32 is provided with a capture reagent that is capable of binding to probes, either uncaptured detection probes or separate calibration probes, which pass through the detection zone 31.

The capture reagents utilized in the calibration zone 32 may be the same or different than the capture reagents used in the detection zone 31. For example, biological capture reagents may be utilized. It may also be desired to utilize various non-biological reagents for the capture reagents. For instance, the capture reagents may include a polyelectrolyte that may bind to probes. The polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly (styryl-b-acrylic acid), both of which are available from Polymer Source, Inc. of Dorval, Canada.

Similar to the detection zone 31, the calibration zone 32 may provide any number of distinct calibration regions in any direction so that a user may better determine the concentration of a particular analyte within a test sample. Each region may contain the same capture reagents, or may contain different capture reagents for capturing different phosphorescent labels. The calibration regions may be pre-loaded on the porous membrane 23 with different amounts of the capture reagent so that a different signal intensity is generated by each calibration region upon migration of the probes. The overall amount of capture reagent within each calibration region may be varied by utilizing calibration regions of different sizes and/or by varying the concentration or volume of the capture reagent in each calibration region. If desired, an excess of detection probes may be employed in the assay device 20 so that each calibration region reaches its full and predetermined potential for signal intensity. That is, the amount of uncaptured detection probes that are deposited upon calibration regions are predetermined because the amount of the capture reagent employed on the calibration regions is set at a predetermined and known level. In the alternative, a predetermined amount of separate calibration probes may be used that are configured to only bind to the capture reagent at the calibration zone 32.

Once captured, the phosphorescent signal of the probes at the detection zone 31 and/or calibration zone 32 may be measured using a phosphorescence reader 50. For example, in this embodiment, the phosphorescence reader 50 is constructed to emit pulsed light simultaneously onto the detection and calibration zones 31 and 32. The reader 50 may also simultaneously receive the phosphorescent signal from the excited labels at the detection and calibration zones 31 and 32. Alternatively, the phosphorescence reader 50 may be constructed to successively emit pulsed light onto the detection zone 31 and the calibration zone 32. In addition, a separate phosphorescence reader (not shown) may also be used to measure the phosphorescent signal at the calibration zone 32.

The construction of the phosphorescence reader 50 may generally vary depending on a variety of factors, such as cost, the level of accuracy required, the nature and concentration of the analyte of interest, and so forth. In one embodiment, for example, a "time-resolved" reader may be utilized. Time-resolved detection involves exciting the phosphorescent label with one or more short pulses of light, then typically waiting a certain time (e.g., between approximately 1 to 100 microseconds) after excitation before measuring the remaining the phosphorescent signal. In this manner, any short-lived phosphorescent or fluorescent background signals and scattered excitation radiation are eliminated. This ability to eliminate much of the background signals may result in sensitivities that are 2 to 4 orders greater than conventional fluorescence or phosphorescence. Thus, time-resolved phosphorescence detection is designed to reduce background signals from the emission source or from scattering processes (resulting from scattering of the excitation radiation) by taking advantage of the phosphorescence characteristics of certain phosphorescent materials.

To function effectively, time-resolved techniques generally require a relatively long emission lifetime for the phosphorescent labels. This is desired so that the label emits its signal well after any short-lived background signals dissipate. Furthermore, a long phosphorescence lifetime makes it possible to use low-cost circuitry for time-gated phosphorescence measurements. For example, phosphorescent labels used in the present invention may have a phosphorescence lifetime of greater than about 1 microsecond, in some embodiments greater than about 10 microseconds, in some embodiments greater than about 50 microseconds, and in some embodiments, from about 100 microseconds to about 1000 microseconds. For instance, platinum (II) coproporhpyrin-I and particles encapsulated with such compounds have an emission lifetime of approximately 50 microseconds, palladium (II) coproporphyrin and particles encapsulated with such compounds have an emission lifetime of approximately 500 microseconds, and ruthenium bipyridyl complexes and particles encapsulated with such compounds have an emission lifetime of from about 1 to about 10 microseconds.

In addition, the phosphorescent label may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of the phosphorescent label to remain far apart from its emission wavelengths and is desirable because a large difference between excitation and emission wavelengths makes it easier to eliminate the reflected excitation radiation from the emitted signal. Further, a large Stokes shift also minimizes interference from phosphorescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the phosphorescent labels have a Stokes shift of greater than about 50 nanometers, in some embodiments greater than about 100 nanometers, and in some embodiments, from about 100 to about 350 nanometers. For instance, platinum (II) coproporhpyrin-I has a Stokes shift of approximately 260 nanometers, palladium (II) coproporphyrin has a Stokes shift of approximately 270 nanometers, and ruthenium coproporphyrin has a Stokes shift of approximately 150 nanometers.

Referring again to FIG. 1, the phosphorescence reader 50 may thus utilize time-resolved detection techniques. In such instances, the reader 50 may include one or more pulsed excitation sources and photodetectors that are in communication with each other and other optional components, such as optical filters. The use of pulsed excitation and time-gated detection, optionally combined with optical filters, allows for specific detection of the phosphorescence from only the phosphorescent label, rejecting emission from other species present in the sample that are typically shorter-lived.

Figure 2:
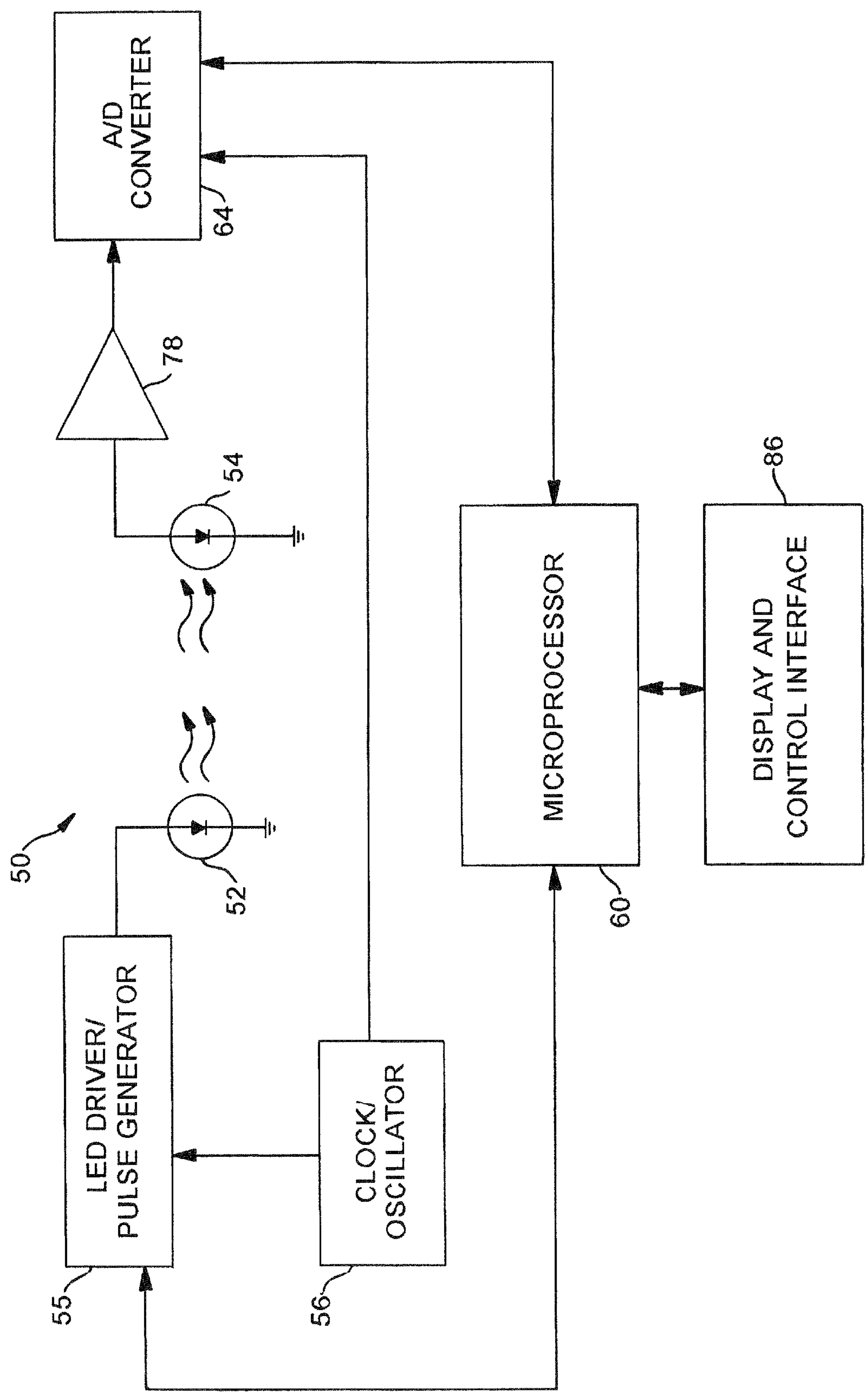
FIG. 2 is a schematic diagram of one embodiment of a phosphorescence reader that may be used in the present invention, including representative electronic components thereof.

For instance, referring to FIG. 2, one embodiment of an exemplary phosphorescence reader 50 is shown that includes an excitation source 52 and a detector 54. Various excitation sources 52 may be used in the present invention, including, for example, light emitting diodes (LED), flashlamps, as well as other suitable sources. Excitation illumination may also be multiplexed and/or collimated; for example, beams of various discrete frequencies from multiple coherent sources (e.g., lasers) may be collimated and multiplexed using an array of dichroic mirrors. Further, illumination may be continuous or pulsed, or may combine continuous wave (CW) and pulsed illumination where multiple illumination beams are multiplexed (e.g., a pulsed beam is multiplexed with a CW beam), permitting signal discrimination between phosphorescence induced by the CW source and phosphorescence induced by the pulsed source. For example, gallium arsenide LED diodes (e.g., aluminum gallium arsenide red diodes, gallium phosphide green diodes, gallium arsenide phosphide green diodes, or indium gallium nitride violet/blue/ultraviolet (UV) diodes) may be used as an illumination source. One commercially available example of a suitable UV LED excitation diode suitable for use in the present invention is Model NSHU55OE (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

Further, examples of suitable detectors 54 that may be used in the present invention include, but not limited to, photomultiplier devices; photodiodes, such as avalanche photodiodes, silicon photodiodes, etc.; high speed, linear charge-coupled devices (CCD), CID devices, or CMOS based imagers; and so forth. In one embodiment, the phosphorescent system utilizes a silicon photodiode for phosphorescent detection. Silicon photodiodes are advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into a system for use in membrane-based devices. If silicon photodiodes are used, then the wavelength range of the phosphorescent emission should be within their range of sensitivity, which is 400 to 1100 nanometers. Another detector option is a CdS (cadmium sulfide) photoconductive cell, which has the advantage of having a spectral sensitivity similar to that of human vision (photopic curve) that may make rejection of the reflected excitation radiation easier.

Optionally, optical filters (not shown) may be disposed adjacent to the excitation source 52 and the detector 54. The optical filters may have high transmissibility in the excitation wavelength range(s) and low transmissibility in one or more undesirable wavelength band(s) to filter out undesirable wavelengths from the excitation source. Undesirable wavelength ranges generally include those wavelengths that produce detectable sample autofluoresence and/or are within about 25 to about 100 nanometers of excitation maxima wavelengths and thus are potential sources of background noise from scattered excitation illumination. Several examples of optical filters that may be utilized in the present invention include, but are not limited to, dyed plastic resin or gelatin filters, dichroic filters, thin multi-layer film interference filters, plastic or glass filters, epoxy or cured transparent resin filters. In one embodiment, the detector and/or excitation source may be embedded or encapsulated within the filter. Although optical filters may be utilized, one beneficial aspect of the present invention is that such filters are often not required as a result of time-resolving. Specifically, due to the delay in phosphorescence emission, emission bandwidth filters may not be required to filter out any short-lived phosphorescence emitted by the excitation source.

Referring again to FIG. 2, various timing circuitry is also used to control the pulsed excitation of the excitation source 52 and the measurement of the emitted phosphorescence. For instance, in the illustrated embodiment, a clock source 56 (e.g., a crystal oscillator) is employed to provide a controlled frequency source to other electronic components in the phosphorescence reader 50. In this particular embodiment, for instance, the oscillator 56 may generate a 20 MHz signal, which is provided to an LED driver/pulse generator 55 and to an A/D converter 64. The clock signal from oscillator 56 to A/D converter 64 controls the operating speed of A/D converter 64. It should be appreciated that a frequency divider may be utilized in such respective signal paths if the operating frequency of A/D converter 64 or if the desired frequency of the clock input to LED driver/pulse generator 55 is different than 20 MHz. Thus, it should be appreciated that the signal from oscillator 56 may be modified appropriately to provide signals of a desired frequency. In some embodiments, a signal from oscillator 56 may also be provided to microprocessor 60 to control its operating speed. Additional frequency dividers may be utilized in other signal paths in accordance with the present invention.

Microprocessor 60 provides control input to pulse generator 55 such that the 20 MHz signal from oscillator 56 is programmably adjusted to provide a desired pulse duration and repetition rate (for example, a 1 kHz source with a 50% duty cycle). The signal from pulse generator 55 may then be provided to the excitation source 52, controlling its pulse repetition rate and duty cycle of illumination. In some embodiments, a transistor may be provided in the signal path to excitation source 52, thus providing a switching means for effecting a pulsed light signal at excitation source 52.

As described above, the pulsed light excites phosphorescent labels associated with the subject assay devices. After the desired response time (e.g., about 100 to about 200 microseconds), the detector 54 detects the phosphorescence signal emitted by the excited phosphorescent labels and generates an electric current representative thereof. This electric current may then be converted to a voltage level by a high-speed transimpedance preamplifier 78, which may be characterized by a relatively low settling time and fast recovery from saturation. The output of the preamplifier 78 may then be provided to the data input of A/D converter 64. Additional amplifier elements (such as a programmable gain amplifier) may be employed in the signal path after preamplifier 78 and before A/D converter 64 to yield a signal within an appropriate voltage range at the trailing edge of the excitation pulse for provision to the A/D converter 64. A/D converter 64 may be a high-speed converter that has a sample rate sufficient to acquire many points within the phosphorescence lifetime of the subject phosphorescent labels. The gain of the preamplifier 78 may be set such that data values drop below the maximum A/D count (e.g., 2047 for a 12-bit converter) on the trailing edge of the excitation pulse. Data within the dynamic range of A/D converter 64 would then be primarily representative of the desired phosphorescence signal. If the sample interval is short compared with the rise-time and fall-time of the excitation pulse, then the gain of preamplifier 78 may be set to ensure that signal values within the upper ½ or ¾ of the dynamic range of A/D converter 78 correspond to the trailing edge of the emission pulse.

A/D converter 64 samples the signal from preamplifier 78 and provides it to the microprocessor 60 where software instruction is configured for various processing of the digital signal. An output from the microprocessor 60 is provided to the A/D converter 64 to further control when the detected phosphorescence signal is sampled. Control signals to preamplifier 78 (not shown) and to A/D converter 64 may be continuously modified to achieve the most appropriate gain, sampling interval, and trigger offset. It should be appreciated that although the A/D converter 64 and the microprocessor 60 are depicted as distinct components, commercially available chips that include both such components in a single module may also be utilized in the present invention. After processing, the microprocessor 60 may provide at least one output indicative of the phosphorescence levels detected by the detector 54. One such exemplary output is provided to a display 86, thus providing a user with a visual indication of the phosphorescence signal generated by the label. Display 86 may provide additional interactive features, such as a control interface to which a user may provide programmable input to microprocessor 60.

Figure 3:
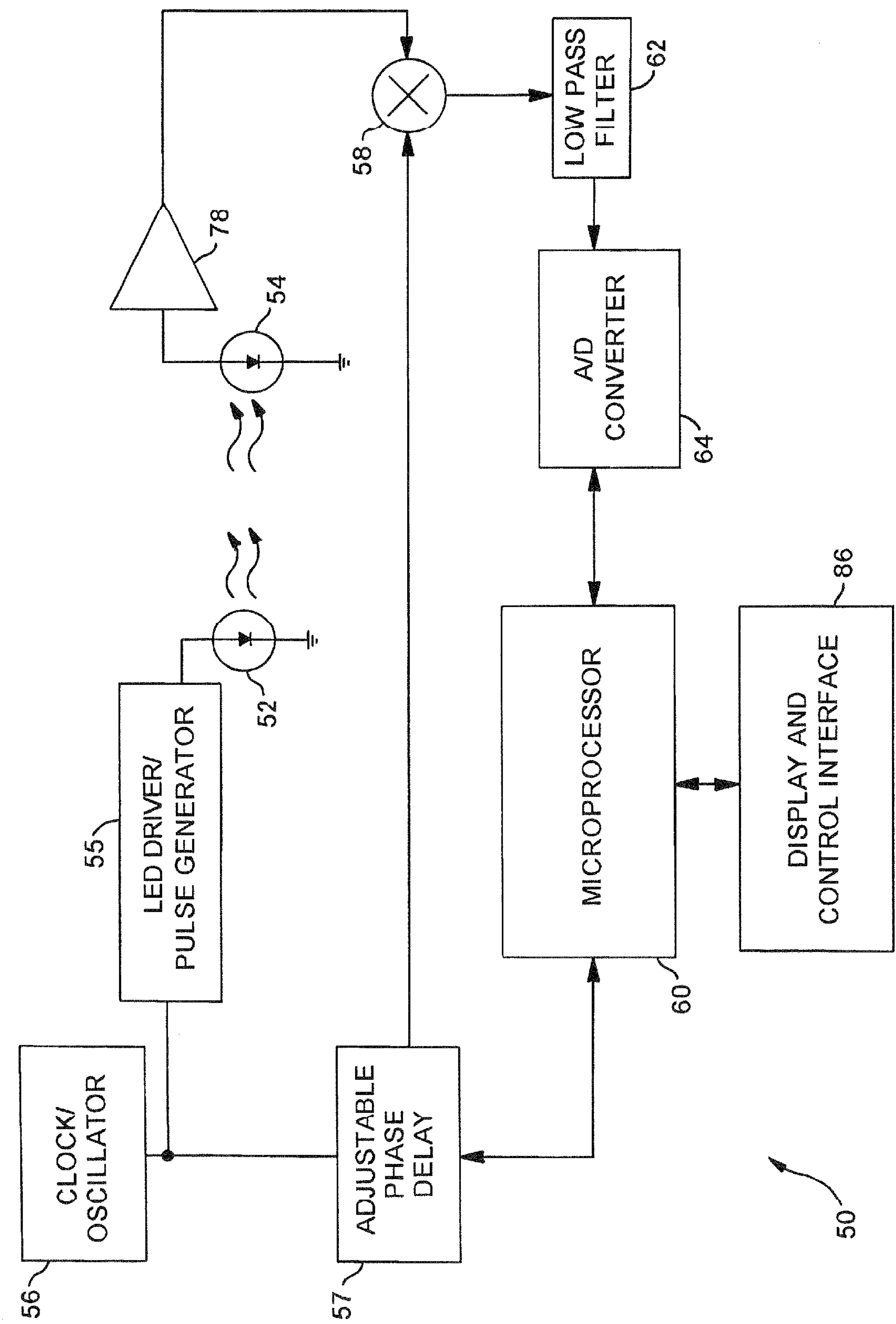
FIG. 3 is a schematic diagram of another embodiment of a phosphorescence reader that may be used in the present invention, including representative electronic components thereof.

Yet another embodiment of representative specific electronic components for use in a phosphorescence reader 50 is illustrated in FIG. 3. Many of the components in FIG. 3 are analogous to those of FIG. 2 and so the same reference characters are used in such instances. For example, one difference in the reader 50 of FIG. 3 as compared to that of FIG. 2 is the generation of a gate signal at phase delay module 57. A control signal from microprocessor 60 is provided to phase delay module 57 to program the effective phase shift of a clock signal provided thereto. This shifted clock signal (also referred to as a gate signal) is then provided to a mixer 58 where such signal is multiplied by the periodic detector signal received by the detector 54 and passed through preamplifier 78. The resulting output of mixer 58 is then sent through a low-pass filter 62 before being provided to A/D converter 64. A/D converter 64 may then measure the output of low-pass filter 62 to obtain a measurement of the phosphorescence during intervals defined by the gate signal.

Figure 4:
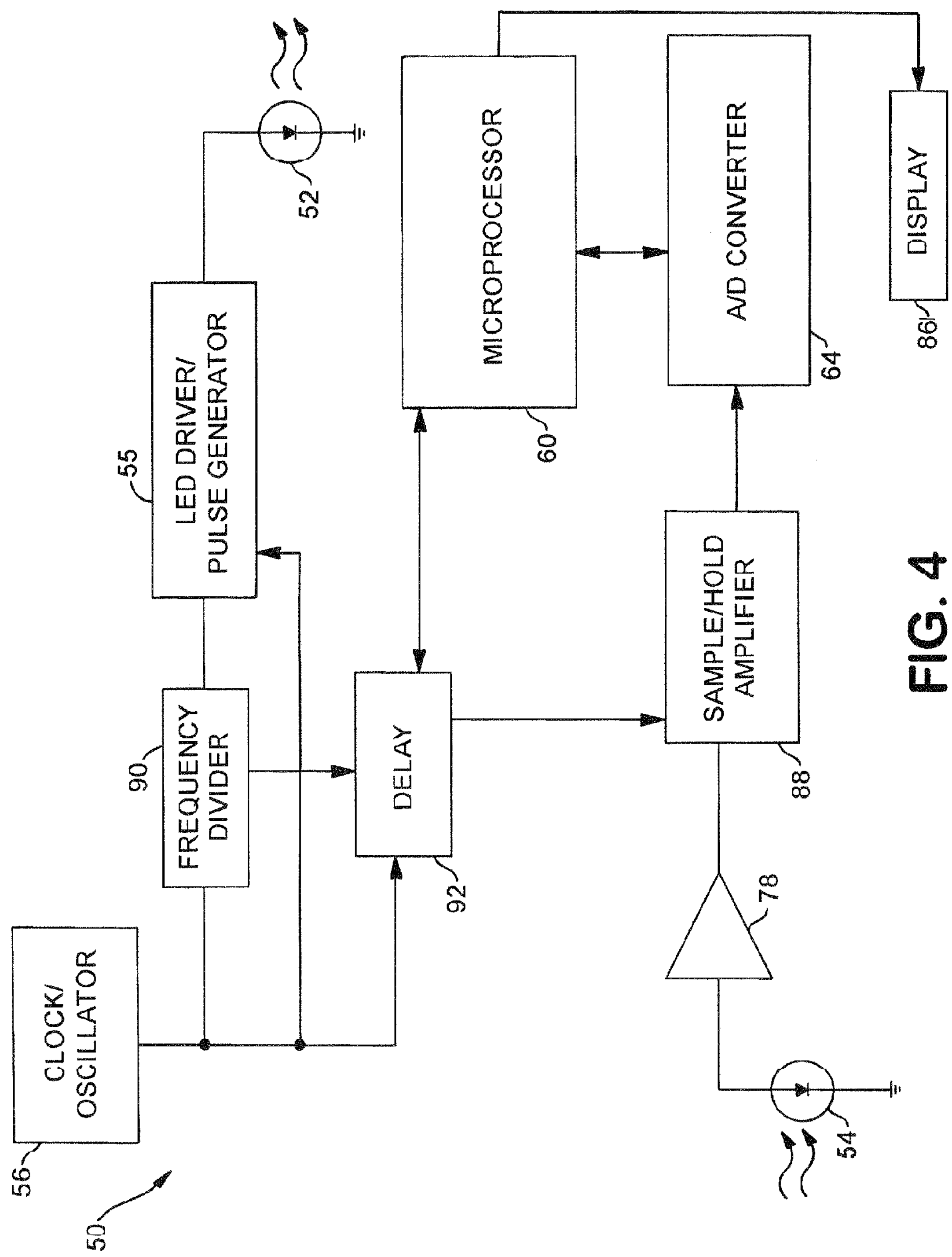
FIG. 4 is a schematic diagram of still another embodiment of a phosphorescence reader that may be used in the present invention, including representative electronic components thereof.

Still further alternative features for an exemplary phosphorescence reader embodiment 50 are illustrated in FIG. 4. For instance, a sample/hold amplifier 88 (also sometimes referred to as a track-and-hold amplifier) is shown that captures and holds a voltage input signal at specific points in time under control of an external signal. A specific example of a sample/hold amplifier for use with the present technology is a SHC5320 chip, such as those sold by Burr-Brown Corporation. The sample/hold amplifier external control signal in the embodiment of FIG. 4 is received from a delay circuit 92, which may, for instance, be digital delay circuit that derives a predetermined delay from the clock using counters, basic logic gates, and a flip-flop circuit. Delay circuit 92 receives a clock signal from oscillator 56 and an enable signal from frequency divider 90, which simply provides a periodic signal at a reduced frequency level than that generated at oscillator 56. Delay circuit 92 may also receive a control input from microprocessor 60 to enable programmable aspects of a delay to ensure proper sampling at sample/hold amplifier 88. The delayed pulse control signal from delay circuit 92 to sample/hold amplifier 88 thus triggers acquisition of the phosphorescence signal from the detector 54 at preset time intervals after the excitation source 52 has turned off.

Regardless of the construction of the reader 50 utilized, the amount of the analyte may be ascertained by correlating the emitted phosphorescence signal, $I_s$, of the labels captured at the detection zone 31 to a predetermined analyte concentration. In some embodiments, the intensity signal, $I_c$, may also be compared with the emitted phosphorescence intensity signal, $I_c$, of labels captured at the calibration zone 32. The phosphorescence intensity signal $I_s$, may be compared to the phosphorescence intensity signal $I_c$. In this embodiment, the total amount of the labels at the calibration zone 32 is predetermined and known and thus may be used for calibration purposes. For example, in some embodiments (e.g., sandwich assays), the amount of analyte is directly proportional to the ratio of $I_s$ to $I_c$. In other embodiments (e.g., competitive assays), the amount of analyte is inversely proportional to the ratio of $I_s$ to $I_c$. Based upon the intensity range in which the detection zone 31 falls, the general concentration range for the analyte may be determined. As a result, calibration and sample testing may be conducted under approximately the same conditions at the same time, thus providing reliable quantitative or semi-quantitative results, with increased sensitivity.

If desired, the ratio of $I_s$ to $I_c$ may be plotted versus the analyte concentration for a range of known analyte concentrations to generate a calibration curve. To determine the quantity of analyte in an unknown test sample, the signal ratio may then be converted to analyte concentration according to the calibration curve. It should be noted that alternative mathematical relationships between $I_s$ and $I_c$ may be plotted versus the analyte concentration to generate the calibration curve. For example, in one embodiment, the value of $I_s/(I_s+I_c)$ may be plotted versus analyte concentration to generate the calibration curve.

As indicated above, sandwich formats, competitive formats, and so forth, may be utilized for the device 20. Sandwich assay formats typically involve mixing the test sample with antibodies to the analyte. These antibodies are mobile and linked to the label. This mixture is then contacted with a chromatographic medium containing a band or zone of immobilized antibodies to the analyte. The chromatographic medium is often in the form of a strip resembling a dipstick. When the complex of the analyte and the labeled antibody reaches the zone of the immobilized antibodies on the chromatographic medium, binding occurs and the bound labeled antibodies are localized at the zone. This indicates the presence of the analyte. This technique may be used to obtain quantitative or semi-quantitative results. Some examples of such sandwich-type assays are described by U.S. Pat. No. 4,168,146 to Grubb, et al. and U.S. Pat. No. 4,366,241 to Tom, et al., which are incorporated herein in their entirety by reference thereto for all purposes.

In a competitive assay, the probe is generally a labeled analyte or analyte-analog that competes for binding of an antibody with any unlabeled analyte present in the sample. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes. Various other device configurations and/or assay formats are also described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

Although various embodiments of device configurations have been described above, it should be understood, that a device of the present invention may generally have any configuration desired, and need not contain all of the components described above.

The present invention may be better understood with reference to the following examples.

EXAMPLE 1

The ability to encapsulate platinum (II) tetra-meso-fluorophenylporphine (Pt (II)-MTPFP) in carboxylated latex particles was demonstrated. Initially, 8 milligrams of a carboxylated latex particle suspension (0.3-micrometer particle size, available from Bangs Laboratories, Inc) was washed twice with ethanol and then suspended in 100 microliters of ethanol. 100 micrograms of Pt (II) MTPFP in 55 microliters of methylene chloride and 45 microliters of ethanol was added to the particle suspension. The mixture was gently shaken for 20 minutes. Then, 100 microliters of water was added. The mixture was then shaken overnight. Approximately 50 vol. % of the solvent was then removed by air stream. 1 milliliter of ethanol was added and centrifuged, after which the supernatant was discarded. The particles were further washed twice with ethanol and then twice with water. The washed particles were suspended by bath sonication in 1.5 milliliter of water for storage. The particles exhibited very strong phosphorescence at an emission wavelength of 650 nanometers when excited at 390 nanometers at ambient conditions (without removing oxygen).

EXAMPLE 2

The encapsulation of platinum (II) tetra-meso-fluorophenylporphine in polyacrylonitrile particles was demonstrated. 118.5 milligrams of polyacrylonitrile and 1.19 milligrams of platinum (II) tetra-meso-fluorophenylporphine were dissolved in 25 milliliters of DMF. 125 milliliters of water was added to the mixture under vigorous stirring. Thereafter, 1 milliliter of a saturated sodium chloride aqueous solution was added to precipitate the dispersed particles. The mixture was centrifuged for 15 minutes and then washed twice with a sodium chloride solution (5 wt. %) and three times with 50 milliliters of water. The residue was then heated for 15 minutes at 70° C. and centrifuged in a phosphate buffer. This procedure is substantially identical to that described in *Bioconjugated Chemistry*, Kurner, 12, 883-89 (2001), with the exception that the ruthenium complexes were replaced with platinum (II) tetra-meso-fluorophenylporphine.

The resulting encapsulated particles exhibited very strong phosphorescence at an emission wavelength of 650 nanometers when excited at 390 nanometers under ambient conditions.

EXAMPLE 3

The ability to conjugate an antibody to phosphorescent particles was demonstrated. The particles were carboxylated latex phosphorescent particles having a particle size of 0.20 micrometers, 0.5% solids, and exhibiting phosphorescence at an emission wavelength of 650 nanometers when excited at a wavelength of 390 nanometers. The particles were obtained from Molecular Probes, Inc. under the name "FluoSpheres."

Initially, 500 microliters of the particles were washed once with 1 milliliter of a carbonate buffer and twice with 2-[N-morpholino]ethanesulfonic acid (MES) buffer (pH: 6.1, 20 millimolar) using a centrifuge. The washed particles were re-suspended in 250 microliters of MES. Thereafter, 3 milligrams of carbodiimide (Polysciences, Inc.) was dissolved in 250 microliters of MES and added to the suspended particles. The mixture was allowed to react at room temperature for 30 minutes on a shaker. The activated particles were then washed twice with a borate buffer (Polysciences, Inc) and re-suspended in 250 microliters of borate buffer. 30 microliters of CRP monoclonal antibody (CRP Mab1) (3.4 milligrams per milliliter, A#5811 from Biodesign) was then added to the particle suspensions. The mixture was allowed to react at room temperature on an end-over-end shaker overnight. During the period of reaction, the suspensions were bath-sonicated twice. The particles were then collected and incubated in 250 microliters of 0.1 molar ethanolamine (Polysciences Inc.) under gentle shaking for 15 minutes. The particles were washed twice with a trizma acid/trizma base buffer (20 millimolar, pH: 7.2). The washed conjugates were suspended in 1 milliliter of the trizma acid/trizma base buffer and stored at 4° C.

EXAMPLE 4

The ability to conjugate an antibody to phosphorescent particles was demonstrated. The particles were carboxylated polyacrylonitrile phosphorescent particles having a particle size of 0.04 micrometers, 0.5% solids, and exhibiting phosphorescence at an emission wavelength of 650 nanometers when excited at a wavelength of 390 nanometers. The particles were obtained from Chromeon GmbH.

Initially, 500 microliters of the particles were suspended in 50 microliters of 2-[N-morpholino]ethanesulfonic acid (MES) buffer (0.1 molar). The particle suspension was bath-sonicated for 5 minutes. Thereafter, 6 milligrams of carbodiimide (Polysciences, Inc.) was dissolved in 50 microliters of MES and added to the suspended particles. The mixture was allowed to react at room temperature for 30 minutes on a shaker. The activated particles were then washed twice with a borate buffer (Polysciences, Inc) and re-suspended in 250 microliters of borate buffer. 30 microliters of CRP monoclonal antibody (CRP Mab1) (3.4 milligrams per milliliter, A#5811 from Biodesign) was then added to the particle suspensions. The mixture was allowed to react at room temperature on an end-over-end shaker overnight. During the period of reaction, the suspensions were bath-sonicated twice. The particles were then collected and incubated in 250 microliters of 0.1 molar ethanolamine (Polysciences, Inc.) under gentle shaking for 15 minutes. The particles were washed twice with a trizma acid/trizma base buffer (20 millimolar, pH: 7.2). The washed conjugates were suspended in 1 milliliter of the trizma acid/trizma base buffer and stored at 4° C.

EXAMPLE 5

The ability to form a lateral flow assay device with using phosphorescent particles was demonstrated. A nitrocellulose porous membrane (HF 120 from Millipore, Inc.) having a length of approximately 30 centimeters was laminated onto supporting cards. Goldline™ (a polylysine solution obtained from British Biocell International) was stripped onto the membrane to form a calibration line. In addition, monoclonal antibody for C-reactive protein (Mab2) (A#5804, available from Biodesign, concentration of 1 milligram per milliliter) was immobilized on the porous membrane to form a detection line. The membrane samples were then dried for 1 hour at a temperature of 37° C. A cellulosic fiber wicking pad (Millipore, Inc. Co.) was attached to one end of the membrane and cut into 4-millimeter half strips.

200 microliters of the conjugated phosphorescent particles of Example 3 (concentration of 2.5 milligrams per milliliter in a trizma acid/trizma base buffer with 1 milligram per milliliter BSA) was applied with 200 microliters of Tween 20 (2%, available from Aldrich) and 200 microliters of sucrose in water (10%). The mixture was bath-sonicated for 20 minutes. The suspension was then loaded onto a 10-centimeter long glass fiber conjugate pad (Millipore Co.). The glass fiber pad was then dried at 37° C. for 2 hours. Thereafter, 600 microliters of Tween 20 (0.5%) was loaded onto a 10-centimeter long glass fiber sample pad (Millipore Co.) and dried at 37° C. for 2 hours. A cellulose wicking pad (Millipore Co.), the sample pad, and conjugate pad were then laminated onto the porous membrane. The laminated full card was then cut into a 4-millimeter wide lateral flow assay device.

EXAMPLE 6

The ability to form a lateral flow assay device with using phosphorescent particles was demonstrated. A nitrocellulose porous membrane (HF 120 from Millipore, Inc.) having a length of approximately 30 centimeters was laminated onto supporting cards. Goldline™ (a polylysine solution obtained from British Biocell International) was stripped onto the membrane to form a calibration line. In addition, monoclonal antibody for C-reactive protein (Mab2) (A#5804, available from Biodesign, concentration of 1 milligram per milliliter) was immobilized on the porous membrane to form a detection line. The membrane samples were then dried for 1 hour at a temperature of 37° C. A cellulosic fiber wicking pad (Millipore, Inc. Co.) was attached to one end of the membrane and cut into 4-millimeter half strips.

The half stick strips were put into a control and test microwell. The control microwell contained 200 microliters of the conjugated phosphorescent particles of Example 4 (concentration of 2.5 milligrams per milliliter in a trizma acid/trizma base buffer), 15 microliters of Tween 20 (2%, available from Aldrich), and 20 microliters of the trizma acid/trizma base buffer. The test microwell contained 200 microliters of the conjugated phosphorescent particles of Example 4 (concentration of 2.5 milligrams per milliliter in a trizma acid/trizma base buffer), 15 microliters of Tween 20 (2%, available from Aldrich), 15 microliters of the trizma acid/trizma base buffer, and C-reactive protein (2 micrograms per milliliter, available from Biodesign).

A half-stick was inserted into each microwell and allowed to develop for 20 minutes. When the assay was finished, the half stick was taken out mounted onto the sample holder of a Fluorolog III Spectrofluorometer (available from SA Instruments, Inc.) using tape. The detection line fit into a rectangular hole in the holder so that the excitation beam would shine directly on the detection line while the rest of the device was remained blocked from the excitation beam. Time-resolved phosphorescence techniques were used. Specifically, the following experiment parameters were used: (1) the angle of the excitation beam to the surface normal of the devices was 70° C.; the detection mode was front face; the slit width was 5 nanometer; (4) the number of scan was 1; (5) the excitation wavelength was 390 nanometers; (6) the emission wavelength was from 600 to 700 nanometers; (7) the sample window was 2 milliseconds (ms); (8) the initial delay was 0.02 ms; (9) the time-per-flash was 50 ms; and (10) the number of flashes was 10.

For the control, the measured phosphorescent intensity was 1.82K (K=1000), while the intensity for the test sample was 8.63K. The phosphorescent intensity was directly related to the quantity of the sandwich complex for the antigen, and therefore directly related to the concentration of the CRP antigen.

EXAMPLE 7

The ability to detect the presence of an analyte using a lateral flow assay device was demonstrated. A nitrocellulose porous membrane (HF 120 from Millipore, Inc.) having a length of approximately 30 centimeters was laminated onto supporting cards. Goldline™ (a polylysine solution obtained from British Biocell International) was stripped onto the membrane to form a calibration line. In addition, monoclonal antibody for C-reactive protein (Mab2) (A#5804, available from Biodesign, concentration of 1 milligram per milliliter) was immobilized on the porous membrane to form a detection line. The membrane samples were then dried for 1 hour at a temperature of 37° C. A cellulosic fiber wicking pad (Millipore, Inc. Co.) was attached to one end of the membrane and cut into 4-millimeter half strips. 200 microliters of the conjugated phosphorescent particles of Example 3 (concentration of 2.5 milligrams per milliliter in a trizma acid/trizma base buffer with 1 milligram per milliliter BSA) was applied with 200 microliters of Tween 20 (2%, available from Aldrich) and 200 microliters of sucrose in water (10%). The mixture was bath-sonicated for 20 minutes. The suspension was then loaded onto a 10-centimeter long glass fiber conjugate pad (Millipore Co.). The glass fiber pad was then dried at 37° C. for 2 hours. Thereafter, 600 microliters of Tween 20 (0.5%) was loaded onto a 10-centimeter long glass fiber sample pad (Millipore Co.) and dried at 37° C. for 2 hours. A cellulose wicking pad (Millipore Co.), the sample pad, and conjugate pad were then laminated onto the porous membrane. The laminated full card was then cut into a 4-millimeter wide lateral flow assay device.

Six (6) of the assay devices were tested. 50 microliters of a mixture of hepes buffer (N-[2-hydroxyethyl]piperazine-N'-(2-ethanesulfonic acid) from Sigma, pH: 7.4) and C-reactive protein were applied to the sample pad. Different concentrations of CRP were tested, i.e., 0, 20, 50, 100, 200 and 1000 nanograms per milliliter. The devices were allowed to develop for 30 minutes. The phosphorescent intensity was measured as described above in Example 6. The intensity at the detection line for CRP concentrations of 0, 20, 50, 100, 200 and 1000 nanograms per milliliter was determined to be 7.21K, 6.03K, 9.31 K, 8.05K, 13.7K, 19.8K, respectively. Thus, as shown, the phosphorescent intensity was directly related to the CRP antigen.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A lateral flow assay device for detecting the presence or quantity of an analyte residing in a test sample, the assay device comprising a porous membrane in fluid communication with detection probes, the detection probes comprising a phosphorescent metal complex encapsulated within a barrier matrix comprising polymethylmethacrylate, the detection probes being conjugated with a specific binding member configured to bind with the analyte and form an analyte complex, wherein the porous membrane defines:

a conjugate pad, the conjugate pad including the detection probes, a detection zone positioned downstream of the conjugate pad within which a capture reagent is immobilized that is configured to bind to the analyte complex to generate a detection signal, and a calibration zone positioned downstream of the detection zone within which a capture reagent is immobilized, the capture reagent being capable of binding to uncaptured detection probes, wherein the analyte is detected by subjecting the detection zone and calibration zone to pulses of light to generate the detection signal and the calibration signal, respectively, and after a certain period of time has elapsed following a pulse of light, the intensity of the detection signal and the calibration signal are measured, the amount of the analyte in the test sample is proportional to a ratio of the intensity of the detection signal to the intensity of the calibration signal.

2. The device as in claim 1, wherein the metal complex comprises a metal selected from the group consisting of ruthenium, osmium, rhenium, iridium, rhodium, platinum, indium, palladium, molybdenum, technetium, copper, iron, chromium, tungsten, zinc, and combinations thereof.

3. The device as in claim 1, wherein the metal complex comprises a ligand selected from the group consisting of pyridine, pyrazine, isonicotinamide, imidazole, bipyridine, terpyridine, phenanthroline, dipyridophenazine, porphyrin, porphine, derivatives thereof, and combinations thereof.

4. The device as in claim 1, wherein the metal complex comprises a porphine complex.

5. The device as in claim 1, wherein the metal complex is selected from the group consisting of platinum (II) tetra-meso-fluorophenylporphine and palladium (II) tetra-meso-fluorophenylporphine.

6. The device as in claim 1, wherein the metal complex comprises platinum (II) tetra-meso-fluorophenylporphine.

7. The device as in claim 1, wherein the metal complex comprises palladium (II) tetra-meso-fluorophenylporphine.

8. The device as in claim 1, wherein the barrier matrix is capable of shielding the encapsulated phosphorescent label from phosphorescence quenchers.

9. The device as in claim 1, wherein the specific binding member is selected from the group consisting of antigens, haptens, aptamers, primary or secondary antibodies, biotin, and combinations thereof.

10. The device as in claim 1, wherein the detection probes are in the form of a particle.

11. The device as in claim 10, wherein the particle is a nanoparticle.

12. The device as in claim 11, wherein the nanoparticle has a diameter of from about 1 nanometer to about 10 microns.

13. The device as in claim 1, wherein the phosphorescent metal complex comprises a phosphorescent label that has a phosphorescent lifetime of greater than about 1 microsecond.

14. The device as in claim 1, wherein the phosphorescent metal complex comprises a phosphorescent label that has a Stokes shift of greater than about 100 nm.

15. The device as in claim 1, wherein the polyelectrolyte capture reagent is a non-biological reagent.

16. The device as in claim 1, further comprising a sampling pad located upstream of the conjugate pad.

17. The device as in claim 1, wherein the capture reagent in the calibration zone is a polyelectrolyte capture reagent.

18. The device of claim 1, wherein the detection zone and the calibration zone are simultaneously subjected to one or more pulses of light.

19. The device of claim 1, wherein the intensity of the detection signal and the intensity of the calibration signal are measured simultaneously.

20. The device of claim 1, wherein the intensity of the detection signal is measured after about 1 to about 100 microseconds.

* * * * *